United States Patent [19]

Stageman

[11] Patent Number: 4,562,245

[45] Date of Patent: Dec. 31, 1985

[54] EXTRACTION PROCESS

[75] Inventor: John F. Stageman, County Durham, England

[73] Assignee: Imperial Chemical Industries PLC, Great Britain

[21] Appl. No.: 600,384

[22] Filed: Apr. 16, 1984

[30] Foreign Application Priority Data

Apr. 28, 1983 [GB] United Kingdom ............... 8311677

[51] Int. Cl.$^4$ ............................................ C08G 63/06
[52] U.S. Cl. .................................. 528/361; 435/135; 528/496
[58] Field of Search ....................... 528/361, 491, 496; 560/185; 260/107; 435/135

[56] References Cited

U.S. PATENT DOCUMENTS

| 3,044,942 | 7/1962 | Baptist . | |
|---|---|---|---|
| 3,275,610 | 9/1966 | Coty | 528/361 X |
| 4,101,533 | 7/1978 | Lafferty | 528/361 X |
| 4,310,684 | 1/1982 | Vanlautem et al. | 528/361 X |
| 4,324,907 | 4/1982 | Senior et al. | 560/185 |
| 4,391,766 | 7/1983 | Barham et al. | 528/361 X |

FOREIGN PATENT DOCUMENTS 15123 3/1980 European Pat. Off. .
58480 8/1982 European Pat. Off. .

OTHER PUBLICATIONS

"Physical Chemistry" by Mee, 5th Ed., 1954, p. 431.
"The Elements of Fractional Distillation" by Robinson et al., 3rd Ed., 1939, p. 14.

*Primary Examiner*—Earl Nielsen
*Attorney, Agent, or Firm*—Cushman, Darby & Cushman

[57] ABSTRACT

A continuous process for the extraction of 3-hydroxybutyrate polymers from micro-organism cells wherein a non-solvent is added to the extracted syrup to permit separation of the polymer and, by distillation, the bulk of the extraction liquid, which may be a solvent/non-solvent mixture, is recovered for re-use. Preferably the non-solvent added to the syrup is also recovered in the distillation.

13 Claims, 1 Drawing Figure

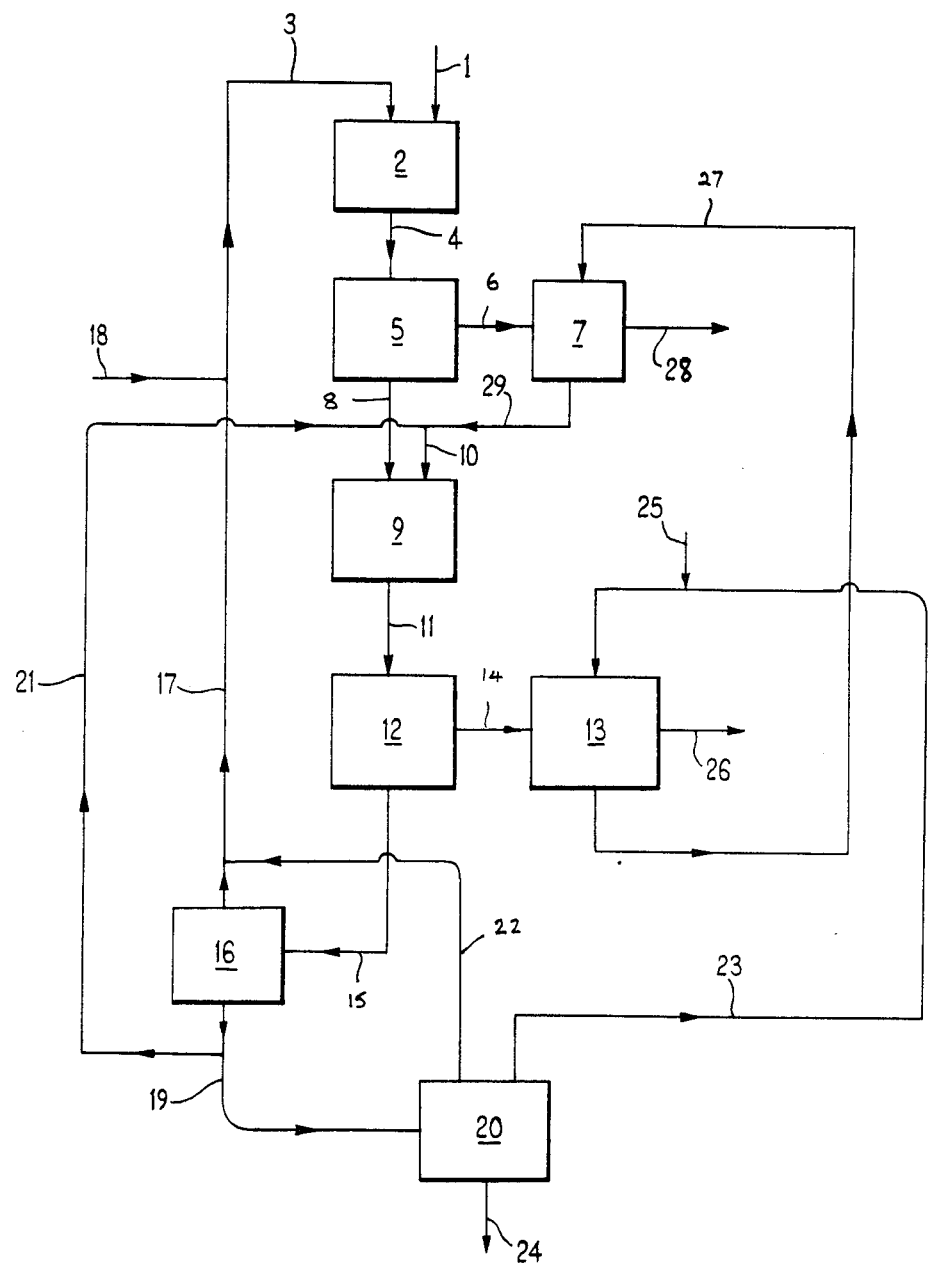

EXTRACTION PROCESS

This invention relates to an extraction process and in particular to the extraction of 3-hydroxybutyrate polymers from micro-organisms.

Poly(3-hydroxybutyrate) is a thermoplastic polyester consisting of repeat units of the formula

—CH(CH$_3$).CH$_2$.CO.O— which is accumulated by many micro-organisms, particularly bacteria, for example of the genera Alcaligenes, Athiorhodium, Azotobacter, Bacillus, Nocardia, Pseudomonas, Rhizobium, and Spirillium, as an energy reserve material.

The polymer is conveniently prepared by cultivating the micro-organism in an aqueous medium on a suitable substrate, such as a carbohydrate or methanol, as an energy and carbon source. The substrate must, of course, be one that is assimilable by the micro-organism. In order to promote accumulation of the polymer, at least part of the cultivation is preferably conducted under conditions wherein there is a limitation of a nutrient that is essential for growth of the micro-organism but which is not required for polymer accumulation. Examples of suitable processes are described in EP-A Nos. 15669 and 46344.

Polymers containing both 3-hydroxybutyrate units and other hydroxycarboxylic acid units, such as 3-hydroxyvalerate units, can also be produced microbiologically. Thus a microbiologically produced heteropolymer containing 3-hydroxybutyrate and 3-hydroxyvalerate residues is described by Wallen et al "Environmental Science and Technology" 8 (1974) 576-9. Also, as described in EP-A Nos. 52459 and 69497 various copolymers can be produced by cultivating the micro-organism on certain substrates, such as propionic acid which gives rise to 3-hydroxyvalerate units in the copolymer.

Accordingly, in the present specification, by the term HB polymer we mean not only the homopolymer, poly(3-hydroxybutyrate), but also copolymers as described above, provided that the 3-hydroxybutyrate residues form at least 40 mole %, and preferably at least 50, mole % of the polymer chain.

While cells containing the polymer can be used as such as a moulding material, for example as described in U.S. Pat. No. 3,107,172, it is generally desirable to separate the polymer from the remainder of the cell material.

Extraction processes that have been proposed involve contacting the cells with an extraction liquid and then the extraction liquid, containing the dissolved HB polymer, is separated from the cell residue. Extraction liquids that have been proposed include various partially chlorinated hydrocarbons such as chloroform, 1,2-dichloroethane, and methylene chloride, and cyclic carbonates such as propylene carbonate, and certain mixtures, e.g. chloroform/methanol (see U.S. Pat. No. 3,275,610) and dichloromethane/ethanol (see U.S. Pat. No. 3,044,942).

In order to obtain good yields, generally the cells are subjected to a cell disruption step to render the cell walls permeable to the extraction solvent. Examples of cell disruption procedures include treatment with acetone (see U.S. Pat. Nos. 3,036,959 and 3,044,942); ultrasonic vibration, grinding, French pressing, freezing/thawing cycles, and lysozyme treatment (see U.S. Pat. No. 3,275,610); flocculation (see EP-A No. 46017); and milling, and spray or flash drying (see EP-A No. 15123). Spray drying is particularly suited to large scale operation.

The extraction processes give a solution of the HB polymer in the extraction liquid. Hereinafter this solution is referred to as the syrup. Unless the syrup is to be used as such, e.g. for casting films, it is necessary to separate the HB polymer from the syrup. Simple evaporation of the extraction liquid from the syrup presents difficulties since the syrup viscosity rises rapidly as the extraction liquid is removed: syrups containing more than about 15% by weight of HB polymers are extremely viscous and difficult to handle.

Separation of the HB polymer by precipitation simply by cooling the syrup is generally not feasible when using the extraction liquids proposed heretofore except where the extraction liquid is a cyclic carbonate. However, cyclic carbonates are relatively expensive and are also high boiling: hence recovery and purification of the extraction liquid for re-use tends to be highly energy consuming. Cooling of syrups made using 1,2-dichloroethane as the extraction liquid can give rise to coherent gels from which the liquid be removed as described in EP-A Nos. 24810 and 58480 or GB-A No. 2120671. However the techniques necessary for obtaining satisfactory gels from 1,2-dichloroethane syrups tend to be time consuming and unsuitable for large scale operation.

In alternative method of separating the HB polymer from the syrup is by precipitation by mixing the syrup with a liquid in which the HB polymer is insoluble but with which the extraction liquid is miscible. Petroleum ether, methanol, and methanol/water mixtures are examples of such precipitants. Again, recovery of the extraction liquid often presents serious difficulties.

We have now found that with certain solvent/non-solvent combinations, extraction of the polymer, separation of the polymer from the syrup, and recovery of the extraction liquid for re-use is relatively simple.

Accordingly the present invention provides a continuous, or cyclic batch, process for the extraction of an HB polymer from dried, solvent-permeable, HB polymer-containing micro-organism cells comprising:
(a) contacting said cells with an extraction liquid to form a syrup containing HB polymer dissolved in the extraction liquid, said extraction liquid containing sufficient of a solvent for said polymer that said extraction liquid dissolves said polymer under the extraction conditions,
(b) separating said syrup from the undissolved cell residue,
(c) treating said syrup by adding thereto a sufficient quantity of a liquid composition, that is miscible with said syrup and that has a lower content of said solvent than said extraction liquid and comprises an organic, non-solvent, liquid or a mixture thereof with said solvent, that said syrup is converted to a composition that can be mechanically separated into a solid polymer phase and a liquid phase, and effecting said mechanical separation,
(d) distilling at least a proportion of said separated liquid phase to recover therefrom a first component consisting of said solvent or a mixture of said solvent and said non-solvent that is richer in said solvent than said liquid phase, and a second component consisting of said non-solvent or a mixture of said solvent and non-solvent that is richer in said non-solvent than said liquid phase, and (e) recycling at least a proportion of said recovered first component to the syrup forming stage, the proportion of said liquid phase that is subject to distillation and of said first component that is recycled being such that at least 80% by weight of said extraction liquid consists of said recycled first component.

In the first stage of the process, the micro-organism cells that have been dried and rendered solvent-permeable, e.g. by spray drying, are contacted with an extraction liquid to form the syrup. For optimum extraction the cells are preferably dried so that their water content is less than 5% by weight. The extraction, or syrup-forming, stage may be conducted at elevated temperatures, preferably above 50° C., but is preferably conducted at a temperature below 125° C. to minimise the risk of thermal degradation of the polymer. To minimise costs of recovery of the extraction liquid, the latter preferably has a boiling point, or boiling range, at atmospheric pressure below 125° C. The extraction should be conducted under conditions such that the cells are contacted with the extraction liquid with the latter in the liquid state, e.g. by refluxing. In some cases it may thus be desirable to operate the extraction step under superatmospheric pressure to maintain the presence of the extraction liquid in the liquid state.

The extraction liquid consists of a solvent for the polymer or a mixture of a solvent and a non-solvent. By the term solvent, we mean a liquid that will dissolve the polymer in the cells under the extraction conditions. Particularly suitable solvents include partially halogenated hydrocarbons such as dichloromethane, chloroform, and 1,2-dichloroethane.

Where the extraction liquid contains a non-solvent, the proportion thereof should be such that, under the extraction conditions, the extraction liquid will dissolve the polymer in the cells. Preferably the extraction liquid contains at least 60% by weight of solvent.

The amount of extraction liquid and the extraction conditions are preferably such that at least 75% by weight of the HB polymer in the micro-organism cells is extracted. The amount of extraction liquid employed will depend on the HB polymer content of the micro-organism cells, the proportion of this polymer that is extracted by the extraction liquid and the desired syrup concentration. The latter should preferably be in the range 1-10% by weight since higher concentrations tend to give syrups that are too viscous for easy separation from the cell residue while lower concentrations may render the formation of the composition from which the polymer phase is mechanically separated difficult.

Preferably, for economic operation, the extraction contact time should be such that the amount of HB polymer that is extracted is at least 80% by weight of the HB polymer that is in the micro-organism cells: typically contact times of 5-60 minutes may be employed. The amount of HB polymer in the micro-organism cells will of course depend on the micro-organism and the cultivation conditions employed: however, for economic operation, the HB polymer content of the cells will normally be at least about 40, preferably at least about 50, % by weight. Thus if the contact time is such that 90% by weight of the HB polymer is extracted, and the cells contain 55% by weight of HB polymer, the amount of extraction liquid required to give syrup concentrations of 1 to 10% by weight will range between about 5 and 50 times the weight of the micro-organism cells.

After forming the syrup, the latter is separated from the undissolved cell residue: this may be effected by conventional centrifugation or filtration techniques.

The syrup is then treated to convert it into a composition, hereinafter termed a separable composition, from which a solid polymer phase can be mechanically separated from the liquid phase. By such separable compositions we include heterogeneous mixtures of a liquid phase and a solid polymer that has been precipitated from the syrup, and gels from which the liquid phase can be mechanically expressed, e.g. by squeezing, as described in aforesaid EP-A No. 24810. Hereinafter the term "strong" gel will be used to mean those gels from which the liquid phase can be so mechanically expressed.

The treatment of the syrups to form the separable composition involves adding to the syrup a sufficient quantity of a liquid composition containing an organic, non-solvent liquid. While this liquid composition may, as hereinafter described, contain some of the solvent, the liquid composition should have a lower solvent content than the extraction liquid. By the term non-solvent we mean a liquid in which the polymer is not soluble to any appreciable extent at the temperature at which the mechanical separation takes place. By "not soluble to any appreciable extent" we mean that a saturated solution of the polymer, prepared by refluxing extracted polymer with the liquid and cooling the solution to the requisite temperature, contains less than 0.1% by weight of the polymer.

The treatment of the syrup to form the separable composition may also include cooling of the syrup. Thus the mechanical separation may be effected at a temperature less than that employed in the extraction stage.

Suitable non-solvents, which must be miscible with the solvent, include methanol, ethanol, acetone, methyl ethyl ketone, and hexane.

The amount of liquid composition added is preferably such that the mixture of the liquid composition and the syrup contains at least 60% by weight of non-solvent.

The technique employed for the mechanical separation step will depend on the nature of the separable composition, e.g. whether it is in the form of a strong gel, or in the form of a heterogeneous mixture. Strong gels can be mechanically separated, as described in aforesaid EP-A No. 24810, by techniques such as squeezing, extrusion, or pressing, while heterogeneous mixtures may be separated by conventional techniques such as centrifugation or filtration.

In some cases it may be desirable to incorporate some water into the liquid added to the syrup in order to give a precipitated polymer in a form that can be more readily separated by filtration or centrifugation. The amount of water in the added liquid should be such that the separated liquid phase contains less than 20, particularly less than 15, % by weight of water.

The added liquid should not contain water if that would render the added liquid non-miscible with the syrup. Water should only be included if the liquid phase can be separated by distillation into a distillate consisting of the solvent or an azeotrope of the non-solvent and the solvent: thus upon distillation of the liquid phase the water forms part of the higher boiling residue.

The mechanical separation gives a solid polymer phase and a liquid phase. At least a proportion of the liquid phase is subjected to distillation to effect recovery of the components thereof. For reasons described hereinafter, it may be desirable to purge from the system part of the liquid phase to prevent a build-up of impurities: however such a purge is preferably effected at a different stage, and so it is preferred that all the liquid phase is subjected to distillation.

Some solvent/non-solvent combinations, e.g. dichloromethane, chloroform or 1,2-dichloroethane with methanol or ethanol, and chloroform with acetone or hexane, give rise to azeotropic compositions on distillation whereas others, e.g. chloroform, dichloromethane, or 1,2-dichloroethane with methyl ethyl ketone, and dichloromethane or 1,2-dichloroethane with acetone or hexane do not.

Where the solvent/non-solvent combination gives rise to an azeotrope, the distillation stage effects separation of the liquid phase into a first component comprising the azeotropic composition and a second component that is richer in the non-solvent than said first component. For reasons described hereinafter it is preferred to select a solvent/non-solvent combination, such as those azeotrope forming combinations mentioned hereinbefore, wherein the azeotrope is the distillate, i.e. the lower boiling fraction.

While of course there are compositions of the solvent and non-solvent that would give, upon distillation, a first component comprising the azeotrope and a second component richer in solvent than the first component, such compositions will generally contain an insufficient proportion of non-solvent to enable mechanical separation of a solid polymer phase from the liquid phase.

Distillation of a preferred system wherein the liquid phase gives rise to a azeotropic distillate leaves as the residue a composition consisting of non-solvent, impurities, and any of the solvent that has not been distilled as the azeotrope. On the other hand, where the azeotrope is the higher boiling i.e. residue component, the impurities will remain in the azeotrope-containing residue.

Where the solvent/non-solvent combination does not give rise to an azeotrope, if the solvent has the lower boiling point, for example in the case of dichloromethane, chloroform, or 1,2-dichloroethane with methyl ethyl ketone, and dichloromethane with acetone or hexane, distillation of the liquid phase causes a first component consisting of the solvent to be distilled off leaving a residue that is richer in the non-solvent than the liquid phase. In this case the extraction liquid can consist solely of the solvent. Likewise if the non-solvent has the lower boiling point, e.g. as in the case of 1,2-dichloroethane with acetone or hexane, distillation of the liquid phase causes the non-solvent to be volatilised leaving a residue that is richer in the solvent than the liquid phase. In this case at least a part of this residue is recycled for use in the extraction liquid.

Preferably the distillation of the liquid phase is conducted so that the distillation is at least 60% complete. Thus, where the solvent, or an azeotrope, is the lower boiling fraction, the first component preferably comprises at least 60% by weight of the theoretical amount of solvent or azeotrope that could be obtained by distillation. Likewise where the non-solvent is the lower boiling fraction, the second component preferably comprises at least 60% by weight of the theoretical amount of non-solvent that could be obtained by distillation.

At least part of the first, i.e. solvent-containing, component recovered from the distillation of the liquid phase is recycled to the extraction step as at least the major part of the extraction liquid. Where the solvent or azeotrope is the lower boiling component, preferably all the recovered first component is recycled. Where no purge is taken from the liquid phase prior to distillation and the second component is the distillate, a purge is preferably taken from the residue, as described hereinafter, to avoid build-up of impurities.

The recycled portion of the first component is used to form at least 80% by weight of the extraction liquid. Preferably at least part of the non-solvent rich second component separated by distillation from the liquid phase is recycled, directly, or indirectly as described hereinafter, to the syrup treatment step.

It will be appreciated that losses of solvent and/or non-solvent, (both accidental losses and deliberate losses, e.g. as a purge) may occur. Suitable make-up quantities of the solvent and non-solvent may be added as necessary at convenient points to compensate for the losses. It is preferred that any make-up quantity of solvent is added to the recycled first component. Hence the extraction liquid will preferably consist of the recycled first component plus such a make-up quantity of solvent as is required to compensate for losses of solvent from the system. Generally the make-up quantities of solvent will be relatively small such that at least 90% by weight of the extraction liquid consists of the recycled first component.

The extraction liquid has to be able to dissolve the polymer in the micro-organism cells. This ability will depend on a variety of factors including the nature and proportions of the solvent and non-solvent (if any), in the extraction liquid, the nature of the polymer, and the extraction conditions, e.g. temperature.

Where an azeotrope is the distillate, the proportions of solvent and non-solvent in the extraction liquid will be determined by the azeotropic composition and the amount of make-up solvent and/or non-solvent added to the recycled first component. Where the non-solvent is the distillate, the proportions of solvent and non-solvent in the extraction liquid will also be determined by the completeness of the distillation: the more complete the distillation, the less non-solvent there will be in the extraction liquid.

The composition of any azeotrope will depend, inter alia, on the pressure at which the distillation is conducted: hence the composition of any azeotrope, and hence that of an extraction liquid containing such an azeotrope, can be varied by employing appropriate distillation conditions.

HB copolymers, particularly those containing HV units, tend to be more soluble than homopolymers; hence an extraction liquid containing a higher proportion of non-solvent can be used when extracting such copolymers than when extracting homopolymer.

Likewise the amount of the non-solvent rich liquid composition that is required to convert the syrup to the separable composition will depend on a variety of factors, including the desired form of the separable composition e.g. strong gel or heterogeneous mixture, the nature of the HB polymer, the nature and proportions of solvent and non-solvent (if any) in the syrup, the mechanical separation conditions, e.g. temperature, and the proportion, if any, of solvent admixed with the non-solvent added to effect the syrup treatment. Thus the liquid added to the syrup to form the separable composition may not consist only of non-solvent: it may contain some solvent.

Where, as is preferred, at least part of the non-solvent rich liquid composition used to treat the syrup is derived from the second component obtained in the distillation stage, in the same way as the composition of the extraction liquid was affected by whether the first component was the distillate and/or the extent of distillation, these factors will also affect the composition of the liquid added to the syrup.

In addition to extraction of the HB polymer from the micro-organism cells, the extraction liquid will also tend to extract lipids and other cell components.

In one form of the invention, the micro-organism cells are subjected to a lipid extraction process prior to contact of the cells with the extraction liquid at the extraction temperature. The solvent used for such a preliminary lipid extraction is herein termed the lipid solvent and should not dissolve the polymer under the lipid extraction conditions. Examples of suitable lipid solvents include methanol and acetone.

After lipid extraction, the polymer-containing cells are separated from the lipid solvent: that lipid solvent can be purified, e.g. by distillation, and recycled if desired. Since the polymer-containing cells remaining after lipid extraction are liable to be contaminated by the lipid solvent, it is preferred that the lipid solvent is the same as the non-solvent employed in the syrup treatment stage, and in many cases, also in the extraction liquid.

In an alternative form of the invention, no preliminary lipid extraction is effected but rather the lipids are coextracted with the polymer by the extraction liquid. When the syrup, which thus contains dissolved lipids as well as the polymer, is subjected to the treatment to form the separable composition, and the polymer phase is mechanically separated from the liquid phase, the lipids will tend to remain in solution in the liquid phase since the non-solvent is generally a solvent for the lipids.

It is therefore desirable, to avoid an undue build-up of lipids in the liquid phase, to subject the liquid phase to a step wherein lipids are separated from the recycled components of the liquid phase. While, as mentioned hereinbefore, this may be effected by purging part of the liquid phase from the system, it is preferred to subject all of the liquid phase to the distillation treatment. The lipids will thus constitute impurities in the residue obtained by distillation of the lipid phase. Part of that residue may simply be discharged as a lipid purge. However it is preferred that part, or all, of that residue is subjected to a second distillation to recover, as the distillate the bulk of the residue from the first distillation for recycle, leaving a residue containing lipids. This lipid-containing residue is discharged as the lipid purge. So that the solvent, which is often more expensive than the non-solvent, can be recovered efficiently, it is preferred that the solvent and non-solvent are selected such that it is the azeotrope or solvent that is the distillate. Hence the lipid purge will contain little or none of the solvent, especially if the distillation step is operated efficiently to volatilise essentially all of the azeotrope or solvent.

This lipid purge represents a "deliberate" loss of non-solvent, and in some cases also of solvent, from the system. In addition to such a deliberate loss, losses of solvent and non-solvent are liable to occur in the separation of the syrup from the cell residue and in the separation of the polymer from the separable composition.

Thus the separated solid polymer phase is liable to have some solvent and non-solvent entrained therewith. Where no lipid extraction step is affected prior to extraction of the cells with the extraction liquid, the liquid entrained with the separated polymer phase will also contain lipids which will contaminate the polymer and may interfere with the properties or processing thereof. It is therefore preferred that the separate polymer phase is subjected to a washing step with a non-solvent rich liquid and the resulting wash liquid is preferably recycled to form at least part of the non-solvent rich liquid composition used to treat the syrup to form the separable composition. The non-solvent used in the washing step may be part or all of the second component recovered from the liquid phase by distillation, alone or with a make-up quantity of the non-solvent. Where the distillation of the liquid phase gives rise to the second component as the residue, which thus contain lipids, the liquid used for the washing is preferably obtained by distillation of the non-solvent from the residue from the first distillation.

The extraction liquid "lost" by entrainment with the separated cell residue may be recovered if desired by distillation of the extraction liquid from the cell residue or by a washing process analogous to that mentioned above in relation to the polymer phase separated from the separable composition. Thus the wash liquid obtained by washing the separated polymer may be used to wash extraction liquid from the cell residue before recycle to the syrup treatment stage.

A preferred form of the invention is further illustrated by reference to the accompanying drawing which is a schematic flowsheet of an extraction process wherein the solvent and non-solvent form an azeotrope that is lower boiling than the non-solvent.

Cells that have been dried and rendered permeable to the solvent, e.g. by spray drying, are fed, via line 1, to an extraction vessel 2. In vessel 2 the cells are contacted with an extraction liquid fed to vessel 2 via line 3. Vessel 2 is maintained at a sufficient temperature to permit the extraction liquid to dissolve the polymer in the cells to form a mixture of a syrup and the residue of the cells. Conveniently the extraction in vessel 2 is effected by refluxing the cells with the extraction liquid. The lipids in the cells are co-extracted with the polymer so that the syrup consists of the extraction liquid having the polymer and lipids dissolved therein.

This mixture of syrup and cell residue is then passed, via line 4, to a separator 5, e.g. a filter or centrifuge, to separate the cell residue from the syrup. The cell residue, carrying with it a small amount of syrup, is discharged via line 6 to a wash vessel 7. The separated remainder of the syrup is then passed, via line 8, to a vessel 9 wherein the syrup is mixed with a non-solvent rich liquid supplied via line 10. The amount of the non-solvent rich liquid added is sufficient to convert the syrup to a separable composition.

The separable composition is passed, via line 11, to a separator 12 wherein the separable composition is separated mechanically into a solid polymer phase and a liquid phase. The solid phase is fed from separator 12 to a wash vessel 13 via line 14. This solid phase will carry with it a little of the liquid phase.

The liquid phase recovered from separator 12 is passed, via line 15, to a still 16 wherein the non-solvent/solvent azeotrope is distilled off leaving a residue consisting of undistilled azeotrope, non-solvent, and the lipids. The distilled azeotrope is fed, via line 17 and a condenser (not shown) to line 3 feeding vessel 2. A make-up quantity of solvent is added, as required, to the recovered azeotrope via line 18.

The residue from still 16 is fed via line 19 to a second still 20. Some of the residue from still 16 may be fed, via line 21, directly to line 10 feeding vessel 9. 0p In still 20 the remainder of the azeotrope, and the bulk of the non-solvent are distilled off. The distilled azeotrope and non-solvent may be collected separately so that the azeotrope is added, via line 22 to that distilled from still 16. Alternatively both the azeotrope and non-solvent distilled from still 20 may be condensed and fed, via line 23 to wash vessel 13.

The residue containing lipids and some non-solvent from still 20 is discharged via line 24 as a lipid purge.

A make-up quantity of non-solvent is added to the non-solvent in line 23 via line 25. In wash vessel 13 the polymer phase separated from the separable composition is washed by the non-solvent, thereby reducing the amount of lipids and solvent entrained therein. The washed polymer is discharged via line 26, while the wash liquid is fed, via line 27, to wash vessel 7. In wash vessel 7, the amount of solvent entrained in the cell residue is reduced and the washed cell residue is discharged via line 28. The wash liquid from vessel 7 is fed to line 10 via line 29.

From this flowsheet it is seen that the amount of solvent lost from the system is very small and so the amount of make-up solvent required from line 18 will be minimal. Losses of non-solvent, made-up via line 25, will however occur as the lipid purge and also entrained with the washed polymer and cell residue.

If desired the cell residue washing can be omitted, with the wash liquid from vessel 13 being fed directly to line 10.

The process of the invention may be operated as a continuous process or as a cyclic batch process. In the latter process a batch of micro-organism cells is subjected to the extraction liquid giving a batch of syrup which is then subjected to the treatment and mechanical separation stages: the batch of liquid phase separated therefrom is then subjected to the distillation process and the first and second components are recovered. The recovered first component, and also, preferably the recovered second component, together with appropriate make-up quantities of solvent and/or non-solvent are then used in the processing of a subsequent batch of cells. It will be appreciated that some stages may be operated as batch processes while others are operated continuously.

The invention is further illustrated by the following example which illustrates the ability of mixtures of methanol and chloroform to act as an extraction liquid.

Spray dried cells Alcaligenes eutrophus NCIB 11599 containing poly(3-hydroxybutyrate) were refluxed with methanol for 15 minutes at atmospheric pressure to extract lipids and then the cells were dried at about 30° C. on trays in an air current.

The dried, lipid extracted, cells contained about 62% by weight of the poly(3-hydroxybutyrate) (PHB).

8 g samples of the lipid extracted cells were refluxed at atmospheric pressure for 30 minutes with 200 ml of various methanol/chloroform mixtures as the extraction liquid. The resultant slurries were filtered hot to remove the cell residues and then the syrups were cooled.

| Run | Methanol content of extraction liquid % by volume | Polymer content of syrup g/l | Gelation characteristics | % PHB extracted (by wt of PHB in lipid extracted cells) |
|---|---|---|---|---|
| A | 0 | 23.5 | Did not gel on cooling to −25 to −30° C. and maintaining at that temperature overnight before warming to room temperature. | 95 |
| B | 30 | 24.1 | | 97 |
| C | 40 | 22.9 | A weak gel was produced on cooling to −25 to −30° C. and maintaining at that temperature overnight before warming to room temperature. After storage at room temperature for 2 days a coherent gel was produced from the weak gel. | 92 |
| D | 45 | 17.7 | Formed a strong gel after cooling to 20° C. and maintaining at that temperature for 4 hours. | 71 |
| E | 50 | 6.1 | Formed a strong gel after cooling to 20° C. and maintaining at that temperature for 2 hours. | 25 |
| F | 100 | 0 | — | 0 |

The syrups of runs A and B could be caused to form strong gels on cooling if sufficient methanol was added to give a composition containing approximately 45% by volume of methanol.

The liquid phase, essentially free from polymer, could then be expressed from the gel by squeezing in a press. Distillation at atmospheric pressure of the expressed liquid phase gave an azeotrope containing approximately 22% by volume of methanol.

The addition of sufficient methanol to the syrups of runs A and B to give compositions containing more than 80% by volume methanol resulted in precipitation of the polymer which could be filtered from the liquid phase. Consequently it is seen that the azeotropic composition could be employed as the extraction liquid in a process of the type illustrated in the aforementioned flowsheet, with either precipitation of the polymer or strong gel formation brought about by the addition of methanol, followed by mechanical separation of the liquid phase from the polymer.

Examples of solvent/non-solvent compositions that may be used, together with their atmospheric pressure boiling characteristics and the practical solvent/non-solvent proportions required to effect extraction under reflux at atmospheric pressure and separation by precipitation of the 3-hydroxybutyrate homopolymer are shown in the following table. If separation is effected by formation of a strong gel and mechanical expression of the liquid phase therefrom, often somewhat larger proportions of solvent in the separable composition can be employed.

| Solvent | Non-solvent | Azeotrope Boiling point (°C.) | Azeotrope Solvent content (wt %) | Practical minimum solvent content of mixture for extraction under reflux at atmospheric pressure (wt %) | Practical maximum solvent content for polymer precipitation (wt %) |
|---|---|---|---|---|---|
| dichloromethane | methanol | 38 | 93 | 76 | 30 |
|  | ethanol | <40 | >95 | 78 | 29 |
|  | acetone | no azeotrope |  | 84 | 30 |
|  | methyl ethyl ketone | no azeotrope |  | 82 | 28 |
|  | hexane | no azeotrope |  | 97 | 44 |
| chloroform | methanol | 53 | 87 | 73 | 32 |
|  | ethanol | 59 | 93 | 80 | 30 |
|  | *acetone | 78 | 64 | 80 | 32 |
|  | methyl ethyl ketone | no azeotrope |  | 75 | 29 |
|  | *hexane | 60 | 84 | 97 | 45 |
| 1,2-dichloroethane | methanol | 61 | 78 | 75 | 28 |
|  | *ethanol | 71 | 63 | 75 | 27 |
|  | acetone | no azeotrope |  | 82 | 28 |
|  | methyl ethyl ketone | no azeotrope |  | 78 | 26 |
|  | hexane | no azeotrope |  | 97 | 41 |

With the exception of the systems marked with an asterisk it is seen that either the non-solvent/solvent mixture can be separated by distillation without azeotrope formation or else the azeotropic composition could be used as such as the extraction liquid. In the case of the combinations marked with an asterisk an appropriate quantity of make-up solvent is required to be added to the azeotropic composition to give a mixture that can be used as the extraction liquid. Additionally, or alternatively, with the combinations marked with an asterisk, extraction temperatures above the atmospheric pressure boiling point of the azeotrope may in some cases enable the azeotrope to be used as the extraction liquid.

I claim:

1. A continuous, or cyclic batch, process for the extraction of a 3-hydroxybutyrate (HB) polymer from dried, solvent-permeable HB-polymer containing microorganism cells, said process comprising:
(a) contacting said cells with an extraction liquid to form a syrup containing HB-polymer dissolved in the extraction liquid, said extraction liquid consisting of a mixture of
 (i) a solvent for said HB-polymer selected from dichloromethane, chloroform, and 1,2-dichloroethane, and
 (ii) a non-solvent for said HB polymer selected from methanol and ethanol, with the proviso that the non-solvent is methanol when said solvent is 1,2-dichloroethane,
said extraction liquid containing sufficient of said solvent that said extraction liquid dissolves said polymer under the extraction conditions,
(b) separating said syrup from the undissolved cell residue,
(c) treating said syrup by adding thereto a sufficient quantity of a liquid composition, that is miscible with said syrup so that said syrup is converted to a composition that can be mechanically separated into a solid polymer phase and a liquid phase, and effecting said mechanical separation, said liquid composition
A. consisting of
 (iii) said non-solvent, or a mixture of said non-solvent and said solvent, and optionally
 (iv) water,
the amount, if any, of water in said liquid composition being such that said separated liquid phase contains less than 20% by weight of water, and
B. having a lower content of said solvent than said extraction liquid,
(d) distilling at least a proportion of said separated liquid phase to recover therefrom the azeotrope formed between said solvent and said non-solvent to leave a residue that is richer in non-solvent than said liquid phase, and
(e) recycling at least a proportion of said recovered azeotrope to the syrup forming stage, the proportion of said liquid phase that is subjected to distillation and of said azeotrope that is recycled being such that at least 80% by weight of said extraction liquid consists of said recycled azeotrope.

2. A process according to claim 1 wherein the extraction liquid has a composition that has a solvent content equal to or greater than that of the solvent/non-solvent azeotrope.

3. A process according to claim 1 wherein all of the azeotrope is recycled to form at least part of the extraction liquid.

4. A process according to claim 1 wherein at least part of the residue is recycled, directly or indirectly, for use as at least part of the liquid composition added to the syrup.

5. A process according to claim 1 wherein all of the separated liquid phase is subjected to said distillation.

6. A process according to claim 5 wherein lipids are coextracted from the micro-organism cells with the HB polymer and part of the residue is discarded as a purge.

7. A process according to claim 6 wherein at least part of the residue is subjected to a further distillation to form a lipid-free distillate and a lipid-containing residue and said lipid-containing residue is that part of the residue obtained by distillation of the liquid phase that is discarded.

8. A process according to claim 1 wherein the separated polymer phase is subjected to a washing step with a liquid rich in said non-solvent, and the wash liquid separated from the washed polymer is recycled for use as at least part of the liquid composition added to the syrup.

9. A process according to claim 8 wherein at least part of the residue obtained by distillation of the liquid phase is recycled and the liquid used to wash the separated polymer phase comprises at least part of that recycled residue.

10. A process according to claim 9 wherein, at least part of the residue is subjected to a further distillation, and at least part of the distillate obtained from said further distillation is used as that part of the recycled residue in the liquid used to wash the polymer.

11. A process according to claim 1 wherein the extraction liquid contains at least 60% by weight of the solvent.

12. A process according to claim 1 wherein the amount of the liquid of lower solvent content than the extraction liquid that is added to the syrup is such that the mixture of that lower solvent content liquid and the syrup contains at least 60% by weight of the non-solvent.

13. A process according to claim 2 wherein the extraction liquid consists of the recycled azeotrope together with that quantity of fresh solvent necessary to compensate for losses of the solvent.

* * * * *